United States Patent [19]

Walker et al.

[11] Patent Number: 4,548,641
[45] Date of Patent: Oct. 22, 1985

[54] HERBICIDES: N,N-DIALKYL-2-(4-SUBSTITUTED-1-NAPHTHOXY) PROPIONAMIDES

[75] Inventors: Francis H. Walker, Mill Valley; Don R. Baker, Orinda, both of Calif.

[73] Assignee: Stauffer Chemical Company, Westport, Conn.

[21] Appl. No.: 497,928

[22] Filed: May 25, 1983

Related U.S. Application Data

[63] Continuation-in-part of Ser. No. 441,701, Nov. 15, 1982, abandoned.

[51] Int. Cl.⁴ .................. C07C 103/26; C07C 103/76; A01N 37/18
[52] U.S. Cl. ........................................ 71/118; 564/172
[58] Field of Search ........................... 564/172; 71/118

[56] References Cited

U.S. PATENT DOCUMENTS

| | | | |
|---|---|---|---|
| 3,480,671 | 11/1969 | Tilles et al. | 260/559 R |
| 3,718,455 | 2/1973 | Baker et al. | 71/118 |
| 3,740,437 | 6/1973 | Harrison et al. | 564/172 X |
| 3,926,613 | 12/1975 | Alt | 71/118 |
| 3,968,145 | 7/1976 | Ghelardoni et al. | 564/172 X |
| 3,998,880 | 12/1976 | Mikailovski et al. | 564/172 |
| 4,266,965 | 5/1981 | Simons | 71/118 |

FOREIGN PATENT DOCUMENTS 1064252  4/1967  United Kingdom .

OTHER PUBLICATIONS

Murphy et al., CA 78: 67889a (1973).

Primary Examiner—Thomas A. Waltz
Attorney, Agent, or Firm—Jeol G. Ackerman

[57] ABSTRACT

Compounds having the formula

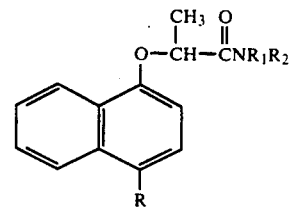

in which R is chloro, fluoro, bromo, methyl, methoxy or methylthio, and $R_1$ and $R_2$ are each $C_1$–$C_4$ alkyl are hebicides. In one embodiment the compound is an optical isomer.

25 Claims, No Drawings

HERBICIDES: N,N-DIALKYL-2-(4-SUBSTITUTED-1-NAPHTHOXY) PROPIONAMIDES

CROSS REFERENCE TO RELATED APPLICATIONS

This application is a continuation-in-part of U.S. application Ser. No. 441,701, filed Nov. 15, 1982, now abandoned.

This invention relates to novel herbicidal compounds having the formula

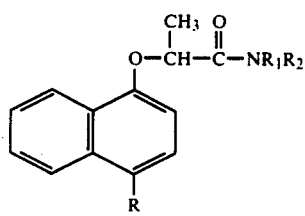

in which R is chloro, fluoro, bromo, methyl, methoxy or methylthio, and $R_1$ and $R_2$ are each $C_1$–$C_4$ alkyl.

The alkyl groups which may be present at the $R_1$ and $R_2$ positions may be the same or different, straight- or branched-chain $C_1$–$C_4$ groups. Such groups include, for instance, methyl, ethyl and the various propyl and butyl moieties. Preferably, both $R_1$ and $R_2$ are straight-chain alkyl groups, including methyl, ethyl, n-propyl or n-butyl. Most preferably at least one of $R_1$ and $R_2$ is methyl or ethyl.

Because of the occurrence of a tetra-substituted carbon atom at the $C_2$ position of the propionamide group, the compounds may exist in either of two optically active forms, or as a racemic mixture of these optically active isomers. This central carbon atom is substituted by a hydrogen atom, a methyl group, a substituted-naphthoxy moiety, and a carbamine group. In a particularly preferred embodiment, the compound is utilized as a herbicide in the levorotary or D-(−) form.

The compounds of this invention have been found to be active herbicides in possessing herbicidal activity against various species of weeds. The compounds have primarily pre-emergence herbicidal activity, against grassy weeds, but they also possess post-emergence activity against both grassy and broadleaf weeds. Some compounds also exhibit pre-emergence activity against broadleaf weeds and control of nutsedge.

This invention also therefore relates to a method for controlling undesirable vegetation, particularly undesirable grassy vegetation, comprising applying to a locus where control of such vegetation is desired, a herbicidally effective amount of a compound as described herein, and also relates to herbicidal compositions of matter comprising a herbicidally effective amount of a compound as described herein, together with an inert diluent or carrier suitable for use with herbicides. As demonstrated, compounds of this invention may be variously advantageously applied prior or subsequent to the emergence of undesirable vegetation at the locus where control is desired.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

The compounds of the present invention may be prepared in any of several ways which are known to be generally suitable for preparation of other types of naphthoxy alkylamides.

In one method, for instance, a 4-substituted-α-naphthol is reacted with a lower alkyl ester of a 2-halopropionic acid (for instance, methyl-2-chloropropionate) in the presence of a base, to produce a 4-substituted-α-naphthoxy propionic acid. The acid is converted to the acyl chloride, for instance by reaction with phosgene, and the acyl chloride is reacted with a dialkylamine having the formula $R_1R_2NH$ ($R_1$ and $R_2$ are as defined above) in the presence of a base to form the final product.

In an alternative method, a 4-substituted-α-naphthol is reacted with an N,N-dialkyl-2-halopropionamide in the presence of sodium methoxide or preferably an aqueous solution of an alkali metal hydroxide such as sodium hydroxide, to produce the resulting amide.

The 4-substituted α-naphthols may be obtained from commercial sources or, if unavailable, may be synthesized according to known methods. For instance, in preparing compounds described in Table I several α-naphthols were not readily available at the time, and were synthesized as follows: 4-fluoro-α-naphthol-from 1-fluoro-4-methoxynaphthalene by the method of Adcock et al., *Journal of the American Chemical Society*, Vol. 98, p. 1701 (1976) (at p. 1703); 4-bromo- α-naphthol-reaction of α-naphthol with iodine monobromide by the method of Militzer, *Journal of the American Chemical Society*, Vol. 60, p. 257 (1938); 4-methylthio-α-naphthol-from α-naphthol and dimethyl sulfoxide, by the method of Goethals et al., *Chemical Abstracts*, 61, 10614a (1964).

In production of optical isomers of compounds of the type described herein, by either of the two processes mentioned above, an optically active intermediate is utilized. In the first process, the optically active intermediate is the lower alkyl ester of the 2-halopropionic acid. For instance, in production of levorotary compounds of the type claimed herein an appropriate intermediate would be L-(+)methyl-2-chloropropionate.

In preparing optical isomers of compounds by the process of the second type (namely reaction of 4-substituted-α-naphthols with an amide), the amide is utilized in an optically active form. Optically active amides of the type involved may be produced, for instance, by reaction of an optically active ester such as L-(+)-methyl-2-chloropropionate with an appropriate dialkylamine in the presence of a reaction promoter selected from the group consisting of Group IIIa metal halides having a molecular weight of 26 or greater and Group IVb metal halides, as disclosed in U.S. Pat. No. 4,358,612 of Richard D. Gless, Jr.

The following are illustrations of the production of compounds according to this invention.

EXAMPLE 1

Preparation of N,N-Diethyl-2-(4'-chloro-1'-naphthoxy) propionamide (Compound 1 herein)

A solution of 6.0 grams (g.) (0.034 mole) of 4-chloro-1-naphthol in 15 milliliters (ml.) tetrahydrofuran was added dropwise to a mixture of 0.9 g. (0.036 mole) of sodium hydride in 50 ml. tetrahydrofuran. One-half hour after the naphthol addition was complete, a solution of 7.1 g. (0.034 mole) of N,N-diethyl-2-bromopropionamide in 15 ml. tetrahydrofuran was added slowly. After addition was complete, the mixture was heated at reflux for ½ hour, then cooled and evaporated. The residue was dissolved in methylene chloride; the solution with suspended sodium bromide was washed successively with 50 ml. portions of water, dilute HCl and saturated salt solution. Removal of the solvent in vacuum, after drying over magnesium sulfate, left a solid, 8.4 g., m.p. 58°-61° C., identified by nuclear magnetic resonance spectroscopy as the title compound. The compound was produced as a racemic mixture of its optical isomers.

EXAMPLE 2

Preparation of D-(−)-N-Methyl-N-(n-propyl)-2-(4'-chloro-1'-naphthoxy) propionamide (Compound 2 herein)

(a) D-(−)-(2-(4'-Chloro-1'-naphthoxy) propionic acid

A solution of 35.0 g. (0.196 mole) of 4-chloro-1-naphthol in 250 ml. toluene was placed in a 500 ml. flask and 16.0 g. (0.440 mole) of sodium hydroxide pellets was added. The mixture was heated with stirring to 85° C. to form the sodium salt of 4-chloro-1-naphthol. After ½ hour at 85° C., the mixture was cooled to 5° C. and then 24.6 g. (0.200 mole) of L-(+)-methyl-2-chloropropionate was added dropwise with stirring at a rate such that the temperature remained between 5 and 10° C. After addition was complete, the reaction mixture was refluxed for six hours. It was then cooled slightly and poured into 300 ml. water. The mixture was stirred well and the pH was adjusted to 2 with concentrated hydrochloric acid. The organic phase was next separated and washed once with 200 ml. of saturated salt solution. Removal of solvent in vacuum after drying left a solid, 18.9 g., m.p. 151°-153° C. This product had an optical rotation of $[\alpha]_D^{25} = -54.38°$ (chloroform).c=4 g/100 ml.

(b) D-(−)-2-(4'-Chloro-1'-naphthoxy) propionyl chloride

A mixture of 18.9 g (0.074 mole) D-(−)-2-(4'-chloro-1'-naphthoxy) propionic acid, and 5 ml. dimethylformamide in 50 ml. dry toluene was heated to 60° C. and phosgene gas was passed into the stirred mixture until 8.4 g. (0.085 mole) had been added. The mixture was added at 60°-65° C. an additional hour and was then purged of residual phosgene and hydrogen chloride by purging the dry nitrogen at 50°-60° C. The solution was decanted from the catalyst and evaporated to leave a liquid, 20.0 g., identified as the propionyl chloride.

(c) D-(−)-N-Methyl-N-(n-propyl)-2-(4'-chloro-1'-naphthoxy) propionamide

A mixture of 1.1 g. (0.015 mole) methyl-n-propylamine, 1.2 g. of 50% aqueous sodium hydroxide (0.015 mole) and 60 ml. toluene was cooled to −5° C. in a dry ice-isopropyl alcohol bath and 4.0 g. (0.015 mole) of D-(−)-2-(4'-chloro-1'-naphthoxy) propionyl chloride was added dropwise with stirring at a rate such that the temperature remained between −5° and 0° C. After addition was complete, cooling was stopped and the mixture was allowed to come to room temperature. The mixture was then washed with 100 ml. each water, dilute HCl, sodium bicarbonate solution and water. The solution was dried over magnesium sulfate, filtered, and evaporated to leave a solid, 4.7 g., m.p. 91°-93° C., identified as the title compound by nuclear magnetic resonance spectroscopy. This product had an optical rotation of $[\alpha]_D^{12} = -137.5°$ (chloroform).c=4 g/100 ml.

The following Table I contains a list of representative compounds of the present invention, prepared as generally described. Structures of all compounds were variously confirmed by infrared, nuclear magnetic resonance, and/or mass spectroscopy.

TABLE I

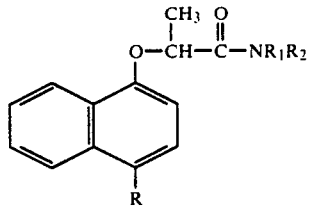

| Compound Number | R | $R_1$ | $R_2$ | Optical Rotation | m.p., °C. or $n_D^{30}$ |
|---|---|---|---|---|---|
| 1 | Cl | $C_2H_5$ | $C_2H_5$ | DL | 58–61 |
| 2 | Cl | $CH_3$ | n-$C_3H_7$ | D-(−) | 91–93 |
| 3 | Cl | $CH_3$ | n-$C_4H_9$ | D-(−) | 60–63 |
| 4 | Cl | $C_2H_5$ | n-$C_3H_7$ | D-(−) | 1.5715 |
| 5 | Cl | $C_2H_5$ | n-$C_4H_9$ | D-(−) | 1.5555 |
| 6 | Cl | $CH_3$ | $C_2H_5$ | D-(−) | 94–97 |
| 7 | Cl | $CH_3$ | $CH_3$ | D-(−) | 126–129 |
| 8 | $OCH_3$ | $C_2H_5$ | $C_2H_5$ | DL | 1.5685 |
| 9 | $SCH_3$ | $C_2H_5$ | $C_2H_5$ | DL | 1.5917 |
| 10 | $OCH_3$ | $CH_3$ | n-$C_3H_7$ | D-(−) | 79–83 |
| 11 | $OCH_3$ | $CH_3$ | n-$C_4H_9$ | D-(−) | 70–74 |
| 12 | $CH_3$ | $C_2H_5$ | $C_2H_5$ | DL | dark oil |
| 13 | F | $C_2H_5$ | $C_2H_5$ | DL | 1.5605 |
| 14 | F | $C_2H_5$ | $C_2H_5$ | D-(−) | 121–126 |
| 15 | F | $C_2H_5$ | $C_2H_5$ | D-(−) | 78–81 |
| 16 | F | $CH_3$ | n-$C_3H_7$ | D-(−) | 58–63 |
| 17 | Br | $C_2H_5$ | $C_2H_5$ | DL | 1.5691 |
| 18 | Br | $CH_3$ | $CH_3$ | DL | 115–122 |

The compounds listed in the foregoing Table I were tested for herbicidal activity as follows:

Pre-Emergence Herbicide Screening Test

Flats were filled with sandy loam soil containing a fungicide and fertilizer. The soil was leveled and rows of three grassy weeds, four broadleaf weeds and yellow nutsedge (*Cyperus esculentus*), were planted thick enough so that several seedlings emerged per inch of row. The grassy weeds were: foxtail (*Setaria spp.*), watergrass (*Echinochloa crusgalli*) and wild oat (*Avena fatua*). Broadleaf weeds utilized were annual morningglory (*Ipomoea purpurea*), velvetleaf (*Alutilon theophrasti*), mustard (*Brassica juncea*), and either pigweed (*Amaranthus retroflexus*), nightshade (*Solanum nigrum*) or curly dock (*Rumex crispus*).

The flats were placed in a greenhouse at 70°-85° F. and watered by sprinkling. One day after planting the flats were sprayed with a solution of a test compound at a rate of 80 gallons of solution per acre with the compound being applied at a rate of 4 pounds per acre (4.48 kg/ha).

The solutions of the test compounds were made by weighing out 300 mg of the compound in question into a 120 ml wide-mouth bottle, dissolving it in 50 ml of acetone containing 1% polyoxyethylene sorbitan monolaurate emulsifier and then diluting to 100 ml with water. Additional solvents, not exceeding 5 ml, were used if needed to dissolve the compound.

The flats were returned to the greenhouse after spraying and watered daily by sprinkling. The degree of weed control was estimated and recorded 3 weeks after treatment, as percentage control compared to the growth of same species in an untreated check flat of the same age.

The percent control is based on the total injury to the plants due to all factors, including inhibited germination, killing of the plant tissue after emergence, stunting, malformation, chlorosis, and othe types of injury. The control ratings vary from 0 to 100 percent, where 0 represents no effect with growth equal to the untreated control, and 100 represents complete kill.

Post-Emergence Herbicidal Evaluation

The soil was prepared and seeded with the same varieties as described for the pre-emergence test. The flats were placed in the greenhouse at 70°-85° F. and watered by sprinkling. Nine to eleven days after planting, the flats were sprayed on a table at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage for three days. Thereafter, they were watered daily by sprinkling. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, four broadleaf weeds, and yellow nutsedge, respectively, in both pre- and post-emergence evaluations.

TABLE II

| Cmpd. No. | Pre-Emergence Control | | | Post-emergence control | | |
|---|---|---|---|---|---|---|
| | grasses | broadleaf weeds | nut-sedge | grasses | broadleaf weeds | nutsedge |
| 1 | 90 | 0 | 0 | 30 | 25 | 10 |
| 2 | 63 | 0 | 0 | 10 | 31 | 0 |
| 3 | 63 | 0 | 30 | 7 | 24 | 0 |
| 4 | 73 | 5 | 0 | 57 | 38 | 0 |
| 5 | 57 | 0 | 0 | 48 | 29 | 0 |
| 6 | 47 | 0 | 0 | 22 | 39 | 0 |
| 7 | 23 | 10 | 0 | 17 | 34 | 0 |
| 8 | 70 | 0 | 0 | 52 | 23 | 0 |
| 9 | 0 | 0 | 0 | 0 | 30 | 0 |
| 10 | 58 | 0 | 0 | 25 | 25 | 0 |
| 11 | 58 | 0 | 0 | 30 | 33 | 0 |
| 12 | 92 | 48 | 0 | 13 | 2 | 0 |
| 13 | 98 | 10 | 50 | 13 | 12 | 0 |
| 14 | 95 | 15 | 40 | 75 | 32 | 90 |
| 15 | 100 | 0 | 60 | 67 | 27 | 70 |
| 16 | 97 | 0 | 0 | 27 | 10 | 0 |
| 17 | 67 | 0 | 0 | 17 | 0 | 0 |
| 18 | 47 | 0 | 0 | 0 | 0 | 0 |

Pre- and Post-emergence Grass Control in Winter Wheat and Winter Barley

Compound 3 was screened at 0.5 and 1.0 lb active ingredient/acre (0.56 and 1.12 kg/ha) for pre- and post-emergence herbicidal activity. Seeds of six plant species were sown in furrows in 108 cubic inch (1650 cubic centimeter) flats containing a loamy sand soil. The grassy weed species included: blackgrass (*Alopecurus myosuroides* Huds.), annual bluegrass (*Poa annua* L.), perennial ryegrass (*Lolium perenne* L.) and wild oats (*Avena fatua* L.). The two crop species included were winter wheat (*Triticum vulgare* L. 'Flanders') and winter barley (*Hordeum vulgare* L. 'Igri').

The test compound was weighed on a Satorius 1265 mp. scale (90 mg.=1 lb/A) into a 60 ml. bottle. The chemical was then put into solution by adding 30 ml. of acetone and 30 ml. water. The acetone had been previously amended with 0.1% of a surfactant (polyoxyethylene sorbitan monolaurate).

The flats were sprayed on the surface with the chemical solution by use of a linear spray table calibrated to deliver a spray volume of 80 gallons per acre, and were immediately moved to a greenhouse and watered by overhead sprinkling. Maximum and minimum air temperatures in the greenhouse during the 12 day test period were 72° F. (25° C.) and 60° F. (15° C.), respectively.

Weed control and crop injury was determined on day 12 after treatment. Visual ratings were based on 0% (no injury) to 100% (complete kill.) Treated flats were compared to untreated control flats.

Results

Compound 3 did not injure wheat or barley at 0.5 or 1.0 lb/A pre- or post-emergence. Grassy weeds were injured pre-emergence, but not post-emergence. The percent growth control for blackgrass, annual bluegrass, perennial ryegrass and wild oats pre-emergence at 0.5 lb/A was 90%, 75%, 90% and 0%, respectively, and at 1.0 lb/A was 95%, 85%, 95% and 0% respectively.

Pre-Emergence multi-weed/multi-crop evaluation

Compounds 12 and 13 were evaluated at application rates of 0.25, 0.5, 1.0 and 2.0 lb. active ingredient/acre (0.28, 0.56, 1.12 and 2.24 kg/ha, respectively) for pre-emergence activity against a number of weed and crop species. The procedure was generally similar to the preemergence evaluation described above. Broadleaf weed species utilized were annual morningglory, velvetleaf, mustard, pigweed, cocklebur (*Xanthium pennsylvanicum*), sesbania (*Sesbania spp.*) and sicklepod (*Cassia obtusifolia*). Grassy weeds utilized were: foxtail, watergrass, wild oat, downy brome (*Bromus tectorum*), annual ryegrass (*Lolium multiflorum*) and shattercane (*Sorghum bicolor*). Yellow nutsedge was also included in these tests. Crops included were: soybean (*Glycine max*), rice (*Oryza sativa*), cotton (*Gossypium herbaceum*), corn (*Zea mays*), wheat (*Triticum aestivum*), milo (*Sorghum vulgare*) and sugarbeets (*Beta vulgaris*).

The following Table III contains the results of these tests, in terms of average control of the seven broadleaf weeds, six grassy weeds, and nutsedge, and injury to the crop species, with visual ratings ranging from 0% (not injury) to 100% (complete kill) as compared to untreated control flats.

TABLE III

| | | | (Pre-emergence Control) | | | | | | | |
|---|---|---|---|---|---|---|---|---|---|---|
| Cmpd. No. | lb/A | Broad-leaf weeds | Grasses | Nut-sedge | Soy-bean | Rice | Cotton | Wheat | Milo | Sugar-beets |
| 12 | 0.25 | 0 | 3 | 0 | 0 | 0 | 0 | 0 | 0 | 0 |
|  | 0.5 | 0 | 17 | 0 | 0 | 0 | 0 | 0 | 20 | 0 |
|  | 1.0 | 0 | 38* | 0 | 0 | 0 | 0 | 0 | 90 | 0 |
|  | 2.0 | 0 | 59* | 0 | 0 | 0 | 35 | 0 | 95 | 0 |
| 13 | 0.25 | 0 | 44 | 10 | 0 | 0 | 0 | 25 | 55 | 0 |
|  | 0.5 | 3 | 73 | 20 | 0 | 20 | 0 | 30 | 75 | 0 |
|  | 1.0 | 9 | 94 | 35 | 30 | 40 | 0 | 35 | 85 | 0 |
|  | 2.0 | 24 | 97 | 100 | 65 | 65 | 0 | 100 | 100 | 20 |

*65% control or greater of watergrass and wild oat.

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid of liquid forms. Examples of solid forms are dusts, granules, tablets, powders and the like. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables, and pastes are obtained by mixing and grinding an active compound with one or more dispersing agents and/or solid carriers or diluents. Also included may be wetting agents and/or dispesing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowable and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of powder dusters, boom and hand sprayers and spray dusters, or applied from airplanes as mists or sprays. When applied in the latter method they may be effective in very low dosages. To modify or control growth of germinating seeds or emerging seedlings liquids compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | | | |
|---|---|---|---|
| Ingredient | Weight % | | |
| Oil | | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 12 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 13 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:

1. A compound having the formula

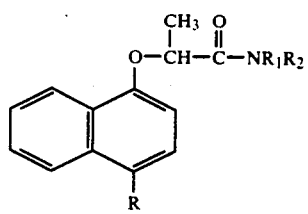

in which R is chloro, fluoro, bromo, methyl, or methoxy and $R_1$ and $R_2$ are each $C_1$–$C_4$ alkyl.

2. A compound according to claim 1 in which $R_1$ and $R_2$ are straight chain alkyl groups.

3. A compound according to claim 2 in which $R_1$ and $R_2$ are identical alkyl groups.

4. A compound according to claim 3 in which $R_1$ and $R_2$ are both ethyl.

5. A compound according to claim 1 in which $R_1$ and $R_2$ are different alkyl groups.

6. A compound according to claim 1 in which R is chloro, $R_1$ is methyl and $R_2$ is n-propyl.

7. A compound according to claim 1 in which R is chloro, $R_1$ is methyl and $R_2$ is n-butyl.

8. A compound according to claim 1 in which R is chloro, $R_1$ is ethyl and $R_2$ is n-propyl.

9. A compound according to claim 1 in which R is chloro, $R_1$ is ethyl and $R_2$ is n-butyl.

10. A compound according to claim 1 in which R is chloro, $R_1$ is methyl and $R_2$ is ethyl.

11. A compound according to claim 1 in which R is chloro, and $R_1$ and $R_2$ are each ethyl.

12. A compound according to claim 1 in which R is chloro, and $R_1$ and $R_2$ are each methyl.

13. A compound according to claim 1 in which R is methoxy, and $R_1$ and $R_2$ are each ethyl.

14. A compound according to claim 1 in which R is methoxy, $R_1$ is methyl and $R_2$ is n-propyl.

15. A compound according to claim 1 in which R is methoxy, $R_1$ is methyl and $R_2$ is n-butyl.

16. A compound according to claim 1 in which R is methyl, and $R_1$ and $R_2$ are each ethyl.

17. A compound according to claim 1 in which R is fluoro, and $R_1$ and $R_2$ are each ethyl.

18. A compound according to claim 1 in which R is fluoro, and $R_1$ and $R_2$ are each methyl.

19. A compound according to claim 1 in which R is fluoro, $R_1$ is methyl and $R_2$ is n-propyl.

20. A compound according to claim 1 in which R is bromo, and $R_1$ and $R_2$ are each ethyl.

21. A compound according to claim 1 in which R is bromo, and $R_1$ and $R_2$ are each methyl.

22. A levorotary optical isomer of a compound according to claim 1.

23. A method of controlling grassy weeds comprising applying to the grassy weeds or the locus thereof a herbicidally effective amount of a compound according to claim 1.

24. A method according to claim 23 in which the compound is applied to the locus prior to the emergence of the grassy weeds.

25. A herbicidal composition comprising: (a) a herbicidally effective amount of a compound according to claim 1 and (b) a herbicidally suitable inert carrier or diluent.

* * * * *